United States Patent [19]

Flowers

[11] 4,258,720
[45] Mar. 31, 1981

[54] STRAIN GAUGE PLETHYSMOGRAPH

[75] Inventor: Edward P. Flowers, Mountain View, Calif.

[73] Assignee: Medasonics, Mountain View, Calif.

[21] Appl. No.: 10,952

[22] Filed: Feb. 9, 1979

[51] Int. Cl.³ .............................................. A61B 5/02
[52] U.S. Cl. .................................. 128/694; 128/721;
128/687; 128/774
[58] Field of Search ...................... 128/694, 686–689,
128/774, 775, 721, 781, 782; 33/DIG. 13;
73/774; 338/2, 6, 47

[56] References Cited

U.S. PATENT DOCUMENTS

| 2,518,906 | 8/1950 | Kocmich | 338/2 X |
|---|---|---|---|
| 3,097,639 | 7/1963 | Streimer | 128/721 |
| 3,268,845 | 8/1966 | Whitmore | 128/721 |
| 3,290,521 | 12/1966 | Coleman et al. | 128/721 |
| 3,332,280 | 7/1967 | Fish et al. | 73/774 |
| 3,520,294 | 7/1970 | Fuzzell et al. | 338/47 X |

OTHER PUBLICATIONS

Hokanson, D. E. et al., *IEEE Trans. on Bio-Med. Engng.*, BME-22, No. 1, Jan. 1975, pp. 25–29.
Youdin, M. et al., *Annals of Bio.-Med. Engng.*, vol. 4, No. 3, Sep. (1976), pp. 220–231.

*Primary Examiner*—Kyle L. Howell
*Attorney, Agent, or Firm*—Warren M. Becker

[57] ABSTRACT

A strain gauge plethysmograph is provided comprising an elastic tubular member (2) filled with a non-mercury electrically conductive gallium-indium alloy which is fluid at room temperature. The tubular member (2) is attached to an inelastic strap member (1) at spaced points (5,6). The length of the strap (1) between the points of attachment (5,6) is limited to approximately 120% of the nominal length of the tubular member (2) for restricting stretching of the tubular member (2).

11 Claims, 7 Drawing Figures

STRAIN GAUGE PLETHYSMOGRAPH

BACKGROUND OF THE INVENTION

The present invention relates to strain gauges in general and in particular to a strain gauge plethysmograph comprising an elastic tubular member. The tubular member is filled with a non-mercury, electrically conductive fluid attached to an inelastic strap member. The strap member is provided for fastening the fluid-filled elastic tubular member to an appendage and for restricting the length to which the tubular member can be stretched when fastened to the appendage.

A typical strain gauge plethysmograph, like the present invention, comprises an elastic tubular member filled with an electrically conductive fluid and means for fastening the tubular member to an appendage. The appendage may comprise an arm, a leg, a finger or the like. Coupled to the tubular member, and in electrical contact with the fluid therein, there is provided a resistance-measuring apparatus, such as a resistance bridge or the like. The resistance bridge is connected to the tubular member and the fluid therein as by relatively small-gauge wires for measuring changes in resistance of the fluid due to blood flow in the appendage.

As the tubular member is stretched lengthwise, the cross section of the tubular member and the fluid contained therein is reduced. This reduction in cross section and increase in length result in an increase in the resistance of the fluid. The magnitude of the increased resistance is a function of the magnitude of the reduction in the cross section and increase in length.

When fastened about an appendage, such as an arm, leg, finger or the like, blood flowing through the appendage will affect the size of the appendage, specifically its circumference, resulting in a corresponding change in the length of the tubular member fastened thereabout. Accordingly, as blood flows into an appendage, the appendage increases in size; and, conversely, as the blood flows from the appendage, the appendage typically decreases in size. Using suitable recording apparatus attached to the tubular member, an operator is able to record both the magnitude and rates of change of blood flow in the appendage.

Heretofore, typical strain gauge plethysmographs used for measuring limb blood flow and blood pressure comprised single or folded rubber tubular members filled with mercury which were wrapped about an appendage. In conventional gauges comprising a folded tubular member the ends of the tubular member are secured to a rigid member adjacent to each other forming a loop in the tubular member. When wrapped about an appendage, the mid-point or center of the loop is fitted over and releasably attached to the rigid member to which the ends of the tubular member are attached somewhat in the fashion of a rubber band.

In gauges using a single tubular member, only one wrap of the tubular member is employed. This arrangement is usually found in the smaller digit gauges.

In practice, a number of disadvantages are associated with using mercury-in-rubber strain gauges. One of the disadvantages is associated with the toxicity of mercury. Because of its toxicity, the use and handling of mercury is considered very dangerous and requires costly methods and apparatus to prevent accidental poisoning of persons using or making devices using it.

Another disadvantage of mercury is associated with its characteristic negative meniscus. Because of this characteristic, mercury tends to draw away from a surface with which it is in contact and is found to separate with age. In a strain gauge, this characteristic is a disadvantage because it is important to form a continuous fluid surface or body end to end with respect to the ends of the gauge.

Another disadvantage of prior known strain gauge plethysmographs is associated with unrestricted stretching of the elastic tubing. Unrestricted stretching of the elastic tubing during fastening of the gauge to an appendage is found to result in the application of undesirable pressure on the appendage and to produce artifact induced changes in the output readings of the gauge. For example, unrestricted stretching of the elastic tubing, especially when using mercury having a negative meniscus, results in such artifacts as separation of the mercury in the tube and bubbles along the surface of the tube at points where the mercury has pulled away from the surface of the tube.

Unrestricted stretching of the tubular member also makes it difficult to obtain reproducible pressures on the limb so that any artifacts which may appear by presence of the apparatus will appear differently from one use of the apparatus to another.

SUMMARY OF THE INVENTION

In view of the foregoing, a principal object of the present invention is a strain gauge plethysmograph which employs an elastic tubular member filled with a non-mercury, electrically conductive fluid at room temperature.

Another object of the present invention is a strain gauge plethysmograph comprising means for restricting the length to which the elastic tubular member of the gauge can be stretched during fastening of the gauge to an appendage.

Still another object of the present invention is a strain gauge plethysmograph in which the means for restricting the stretching of the gauge apparatus is also employed for fastening the apparatus to an appendage.

In accordance with the above objects, a principal feature of the present invention is the use of a non-mercury electrically conductive fluid comprising a gallium indium alloy.

Another feature according to the above objects of the present invention is an inelastic strap to which the tubular member comprising the gallium indium alloy is attached at spaced points for preventing stretching of the tubular member beyond approximately 120% of its nominal length.

By using a gallium indium alloy problems associated with the use of mercury are avoided and by using an inelastic strap for mounting the tubular member, problems associated with induced artifacts are avoided.

BRIEF DESCRIPTION OF THE DRAWINGS

The above and other objects, features and advantages of the present invention will become apparent from the following detailed description of the accompanying drawings in which.

DETAILED DESCRIPTION OF THE DRAWINGS

Figure 1:
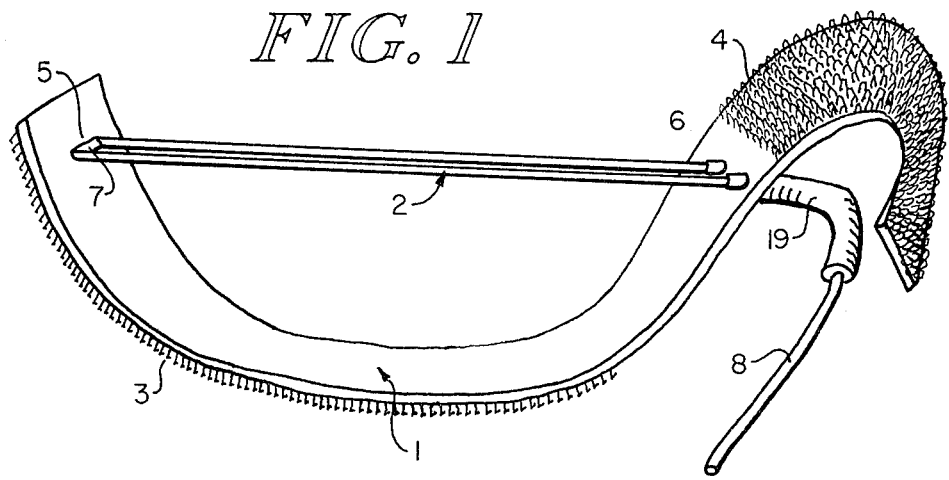
FIG. 1 is a perspective view of a gauge according to the present invention.

Referring to FIG. 1, there is provided an elongated inelastic strap member designated generally as 1 and an elastic tubular member 2. The strap member 1 is provided on one side thereof with a plurality of hook-shaped members 3. The hook-shaped members 3 cover the exterior surface of the strap 1 and extend from one end thereof past the mid-point thereof. On the opposite inside surface of the strap 1 there is provided a plurality of loop members which extend from a point corresponding to the end of the field of hook members 3 to the opposite end of the strap member 1. The hooks 3 are provided for releasably engaging the loops 4 in a conventional manner. Commercially available straps of material comprising hooks and loops as described are commonly known as Velcro strap material. To form the strap of FIG. 1, a strap of hooks and a strap of loops of commercially available material may be attached back-to-back.

The elastic tubular member 2 is folded at its center and attached to the strap 1 at two spaced points 5 and 6. At the point 5, there is provided a short length of tubular material 7. The tube 7 is provided with an inner diameter slightly larger than the outer diameter of the tubular member 2 for attaching the tubular member 2 to the strap 1 at point 5 without pinching it. At the point 6 the ends of the tubular member 2 are fitted with wires and a cable 8 and attached to the strap 1 as by cement or the like, as will be further described with respect to FIG. 2. The cable 8 is provided for connecting the tubular member 2 to a resistance-measuring apparatus, as will be further described with respect to FIG. 6.

Figure 2:
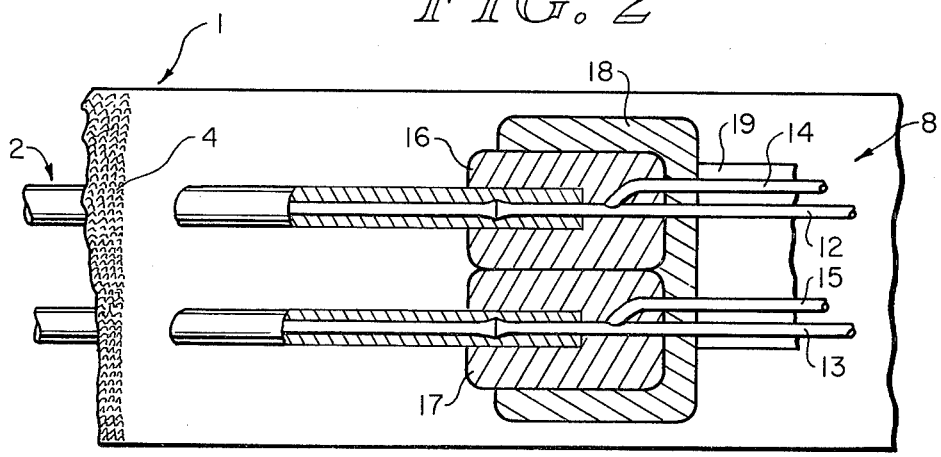
FIG. 2 is an enlarged cross-sectional view of a portion of the gauge of FIG. 1.

Referring to FIG. 2, the size of the strap member 1 and the tubular member 2 depends on the size of the appendage on which the gauge is intended to be used. Typically, there are two sizes. The digit gauge for use on a finger or toe typically comprises tubing with an inner diameter of 12 mils and an outer diameter of 20 mils. A larger gauge for use on an appendage the size of an arm or a leg typically comprises a tubular member having an inner diameter of 20 mils and an outer diameter of 37 mils. The width and length of the strap member 1 and the length of the tubular member 2 is sized correspondingly to fit about the appendage on which the gauge is fastened. As will be apparent, when wrapped about an appendage, the tubular member 2 may overlap without impairing the accuracy of the measurements made therewith.

After being filled with a gallium indium alloy, a pair of wires or electrodes 12 and 13 are fitted in the ends of the tubular member 2 for electrical contact with the gallium indium alloy. In all cases, the outer diameter of the wires 12 and 13 is larger than the inner diameter of the tubular member 2 so as to provide a snug fluid-tight seal therewith. For example, in the smaller digit gauge using a tubular member 2 having an inner diameter of 12 mils, the size of the wire is 18 mils. In the larger tubular member having an inner diameter of 20 mils, the size of the wire is typically 32 mils.

The wires 12 and 13 are current-carrying wires. Coupled to the wires 12 and 13, respectively, as by soldering, there are provided sense wires 14 and 15. As will be apparent, the sense wires 14 and 15 are employed for measuring the voltage drop across the tubular member 2. To form a tight fit and seal the wires 12 and 14 to the tubular member 2 and the wires 13 and 15 to the tubular member 2, each end of the tubular member 2 and its associated wires is individually sealed by means of a thermoplastic shrink sleeve 16 and 17. The sleeves 16 and 17 are, in turn, sealed in a thermal shrink sleeve 18 for additional mechanical sealing and protection against separation of the components. In addition to the sleeves 16, 17 and 18, the wires 12, 13, 14 and 15 are enclosed in a wrapping 19 for forming the cable 8.

Figure 3:
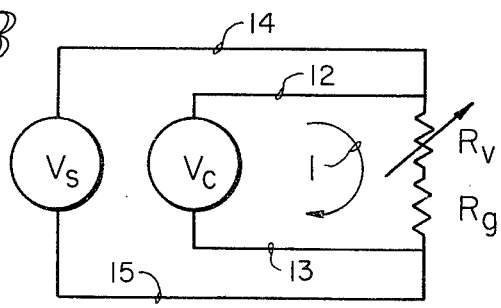
FIG. 3 is a schematic representation of an electrical circuit associated with the apparatus of the present invention.

Referring to FIG. 3, there is shown a schematic of the gauge of the present invention in which a resistance $R_G$ represents the resistance of the tubular member 2. The ends of the tubular member 2 are coupled to a voltage source $V_C$ by means of the wires 12 and 13 for providing a current I in the tubular member 2. A variable resistor $R_V$ is shown to represent the change in resistance corresponding to a change in the length and cross section of the tubular member 2 as the tubular member 2 is stretched and relaxed by blood flow in an appendage. Across the gauge, and specifically across the variable resistance $R_G+R_V$, there is connected, by means of the sense wires 14 and 15, a voltmeter or the like $V_S$. The voltmeter $V_S$ is provided for measuring the voltage drop, and more specifically the changes in voltage drop, across the tubular member 2, as represented by the variable resistance $R_G+R_V$. As will be apparent, the utilization of sense wires 14 and 15 avoids artifacts associated with resistance in the wires since there is no appreciable current through the wires.

Figure 4:
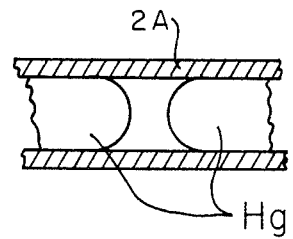
FIG. 4 is a representative drawing of the negative meniscus characteristic of mercury.
Figure 5:
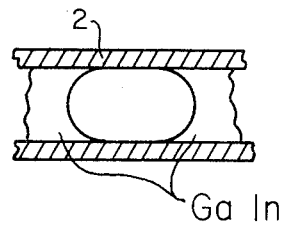
FIG. 5 is a representative drawing of the positive meniscus characteristic of a gallium-indium alloy used in the present invention.

Referring to FIGS. 4 and 5, there is shown in cross section a tubular member 2a containing mercury and the tubular member 2 containing the gallium-indium alloy. As seen in FIG. 4, mercury having a characteristic negative meniscus, tends to draw away from the surface of the tubular member 2a, whereas, as shown in FIG. 5, the gallium-indium alloy, having a positive meniscus, tends to wet the interior of the tubular member 2. Because of this difference in surface tension, the gallium indium alloy is preferable to mercury for use in the gauge of the present invention because it opposes any attempts to separate and thereby reduces artifact-induced changes in the readings of the gauge. A further important advantage of the gallium-indium alloy is associated with its containing no mercury and therefore much safer to handle in the manufacture and use of the gauges.

As previously indicated, the tubular member 2 is attached to the strap 1 at points 5 and 6. To insure that the tubular member 2 is snugly fitted about an appendage when the gauge is fastened to the appendage, the tubular member 2 is provided to have a nominal length somewhat shorter than the length of the strap 1 between the attachment points 5 and 6. Conversely, the difference between the nominal length of the tubular member 2 and the length of the strap 1 between the attachment points 5 and 6 is restricted to approximately 20% of its nominal length. This is done so as to restrict the stretching of the tubular member 2 to less than 20% of its nominal length. By restricting the stretching of the tubular member 2 to less than 20% of its nominal length, artifact-induced changes caused by pinching of the tubular member 2 and inadvertent separation of the gallium indium alloy are avoided.

Figure 6:
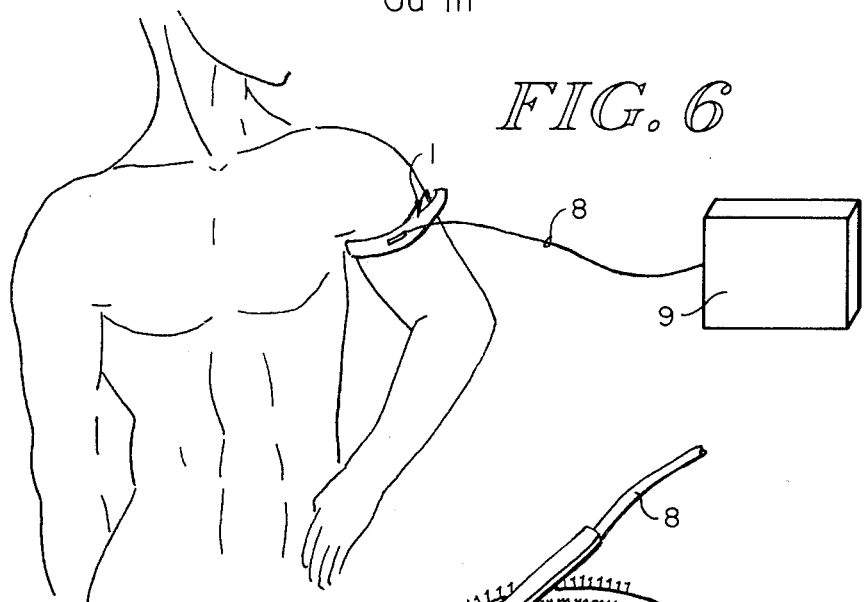
FIG. 6 is a representative drawing of the use of the present invention on an appendage.
Figure 7:
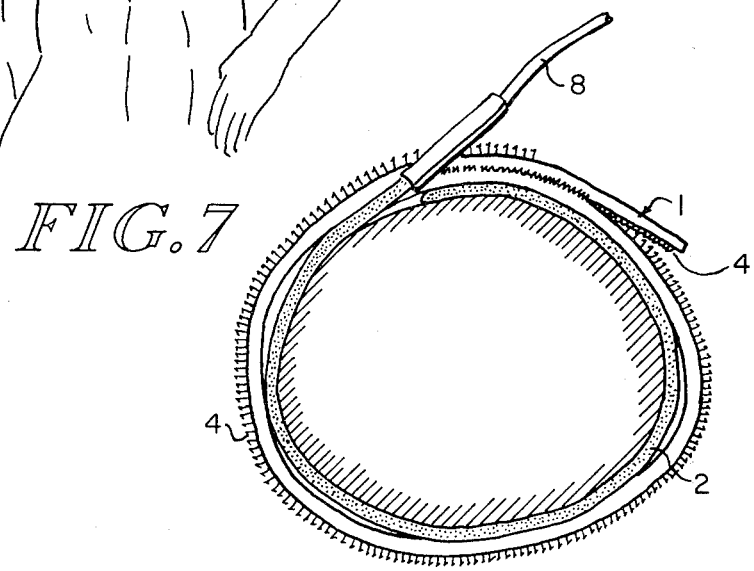
FIG. 7 is a cross-sectional representation of the appendage of FIG. 6.

Referring to FIGS. 6 and 7, in use the gauge 1 is wrapped about an appendage with the gallium indium alloy filled tubular member 2 placed snugly against the appendage surface with the loop side of the strap 1 facing inwardly in facing relationship with the hook side of the strap member. In this manner, one end of the strap member is secured to the outer surface of the strap member. The exterior end of the cable 8 is connected to a resistance-measuring apparatus 9. With the gauge connected to the resistance-measuring apparatus 9, blood flowing in the appendage will cause the diameter of the appendage to change, resulting in a stretching and relaxing of the tubular member 2. As the tubular member 2 stretches and relaxes, its resistance changes. The changes in resistance are displayed on suitable meters or recording apparatus in the resistance-measuring apparatus 9.

While a specific embodiment of the present invention is described, it is contemplated that various changes and modifications to the embodiments may be made without departing from the spirit and scope of the present invention. For example, tubular member 2 is shown folded at its center with its center portion connected at point 5 and its adjacent ends connected at point 6 to the strap 1. It is well within the scope of the present invention to mount the tubular member 2 to a strap without folding it so that the wires connecting the tubular member 2 to the resistance-measuring apparatus 9 extend from opposite ends of the strap 1. It will also be appreciated by those skilled in the art that the number of sections of tubular member 2 wrapped about an appendage does not affect the accuracy of the resistance changes being measured. On the other hand, the folding of the tubular member 2 in the manner described is preferable in many applications.

It will also be appreciated that a Velcro type strap is not required but that any strap material may be used and can comprise any suitable buckle or the like.

Accordingly, it is intended that the present invention be not limited to the embodiments described herein, but rather be determined by reference to the claims hereinafter provided and their equivalents.

What is claimed is:

1. A transducer for a strain gauge plethysmograph comprising:
    an elastic tubular member;
    electrically conductive means;
    means for fastening said elastic tubular member about an appendage; and
    means coupled in parallel with said elastic tubular member for mechanically restricting the length to which said elastic tubular member can be stretched when it is fastened about said appendage.

2. A transducer for a strain gauge plethysmograph according to claim 1 wherein said means for fastening the elastic tubular member about an appendage and said means for restricting the length to which said elastic tubular member can be stretched about an appendage comprises a substantially inelastic strap member and means for attaching said elastic tubular member to said inelastic strap member.

3. A transducer for a strain gauge plethysmograph according to claim 2 wherein said elastic tubular member has a nominal length when unstretched and said means for attaching comprises means for attaching said tubular member to two points on said strap member which are separated by a predetermined percentage of said nominal length.

4. A transducer for a strain gauge plethysmograph according to claim 3 wherein said predetermined percentage is approximately 120%.

5. A transducer for a strain gauge plethysmograph according to claim 2 wherein said tubular member is folded at its center with its ends located adjacent to each other and said attaching means comprises means for attaching said elastic tubular member to said inelastic strap member so that the ends of the tubular member are attached to said strap member adjacent to each other and said center of said tubular member is attached to said strap member a predetermined distance along said strap member from said ends.

6. A transducer for a strain gauge plethysmograph according to claim 5 wherein said predetermined distance is approximately 120% of the nominal length of said elastic tubular member.

7. A transducer for a strain gauge plethysmograph according to claim 2 wherein said means for attaching said tubular member to said strap member permits said tubular member to be stretched a selected distance up to a predetermined distance about said appendage with said elastic tubular member located on the interior of said inelastic strap member relative to the surface of said appendage and means for removably attaching one part of the inelastic strap member to a second part thereof when the elastic tubular member is stretched said selected distance about said appendage.

8. A transducer for a strain gauge plethysmograph according to claim 7 wherein said means for attaching said inelastic strap member to itself comprises a first portion with hooks and a second portion with loops, said loops and said hooks being provided for releasable engagement.

9. A strain gauge plethysmograph comprising:
    an elastic tubular member filled with a mercury-free metallic electrically conductive fluid having a positive meniscus at room temperature;
    means for fastening said tubular member about an appendage so that the resistance of said conductive fluid in said tubular member changes as a function of blood volume in said appendage; and means for electrically coupling said fluid at each end of said tubular member to an apparatus for providing an output corresponding to said changes in the resistance of said conductive fluid.

10. A transducer for a strain gauge plethysmograph according to claim 9 wherein said fluid in said elastic tubular member is a gallium-indium alloy.

11. A transducer for a strain gauge plethysmograph according to claim 10 wherein the ends of said elastic tubular member comprise an inner diameter and said electrical coupling means comprises means forming an electrical conductor for forming an electrical connection with said gallium-indium alloy located therein, said conductor having an outer diameter greater than the inner diameter of said elastic tubular member for forming a fluid-tight seal therewith.

* * * * *